United States Patent [19]

Retallick

[11] Patent Number: 5,487,869
[45] Date of Patent: Jan. 30, 1996

[54] AIR CLEANER CAPABLE OF CATALYTIC REGENERATION

[76] Inventor: William B. Retallick, 1432 Johnny's Way, West Chester, Pa. 19382

[21] Appl. No.: 126,183

[22] Filed: Sep. 24, 1993

[51] Int. Cl.$^6$ .............................. A61L 9/16; B01D 50/00; F01N 3/10
[52] U.S. Cl. ................ 422/22; 422/122; 422/169; 422/171; 422/174; 95/148; 96/126; 96/130; 96/154
[58] Field of Search ................... 95/148; 96/126, 96/130, 152, 154; 55/520; 422/178, 174, 171, 177, 170, 173, 211, 212, 122, 22, 4, 169

[56] References Cited

U.S. PATENT DOCUMENTS

| | | | |
|---|---|---|---|
| 4,741,882 | 5/1988 | Weichselgartner | 422/122 |
| 4,911,894 | 3/1990 | Retallick et al. | 422/174 |
| 4,928,485 | 5/1990 | Whittenberger | 422/180 X |
| 4,976,929 | 12/1990 | Cornelison et al. | 422/174 |
| 5,070,694 | 12/1991 | Whittenberger | 422/174 X |
| 5,140,811 | 8/1992 | Minami et al. | 422/169 X |
| 5,252,299 | 10/1993 | Retallick | 55/520 X |
| 5,269,140 | 12/1993 | Take et al. | 422/171 X |
| 5,271,906 | 12/1993 | Yuuki et al. | 422/171 X |

Primary Examiner—Robert J. Warden
Assistant Examiner—E. Leigh Dawson

[57] ABSTRACT

An air cleaner includes first and second support structures connected in series. The first support structure has a coating made of a material which absorbs organic contaminants from air passing through it. A combustion catalyst coats the second support structure. The air cleaner thus removes organic contaminants from the air at ambient temperature, when air passes through the first support structure. When the air cleaner has operated for an extended time, the absorbent coating becomes filled with contaminants. One then regenerates the air cleaner by applying heat to both support structures, to evolve the organic contaminants from the first support structure and to burn off these contaminants catalytically in the second support structure. In one embodiment, the support structure has the form of an electrically heated converter, in which one uses an electric current to provide the heat needed for regeneration. Only a relatively small volume of air becomes heated during regeneration. A suitable system of valves and sensors assures that air flows through the desired paths during the cleaning and regeneration phases. Other embodiments of the invention include a single support structure, which may or may not have a catalyst coating.

29 Claims, 3 Drawing Sheets 5,487,869

AIR CLEANER CAPABLE OF CATALYTIC REGENERATION

BACKGROUND OF THE INVENTION

This invention relates to the field of air cleaners, and provides an air cleaner which regenerates itself by catalytic combustion.

In a closed space such as the interior of a spacecraft or a submarine, it becomes important to purify the air with minimal expenditure of energy, and with devices that occupy very little space. Furthermore, no make-up air can be brought in from the outside, and all of the cleaned air must be returned to the closed space. U.S. Pat. No. 4,911,894 describes in detail the theory of operation of a spirally-wound catalytic air cleaner. This specification hereby incorporates by reference the disclosure of the above-cited patent. In the above-cited patent, one forms the air cleaner from two strips of metal foil, wound together to form a double spiral. The double spiral defines two flow channels, one leading into the core of the spiral, and the other leading out. A combustion catalyst coats the strips of foil. The incoming air stream receives heat by heat exchange with the outgoing air stream, and also from a heater located in the core of the spiral. Catalytic combustion occurs on the surfaces of the strips.

The present invention provides an alternative arrangement, in which the cleaning of the air occurs entirely at ambient temperature, without expenditure of electrical energy and without combustion. Instead, one expends energy only during a periodic regeneration phase, at which time one uses catalytic combustion to remove impurities absorbed by the cleaner.

For cleaning the air in a passenger airliner, the air cleaner is simpler. The cleaning process is the same as described above, but there is no catalytic combustion and no heat exchange. Instead, the impurities are rejected to the outside of the airliner, and make-up air is brought in from the outside.

SUMMARY OF THE INVENTION

In one embodiment, the present invention includes a first support coated with a material which absorbs impurities in the air, and a means for heating this coated support. There is a second support which is coated with a combustion catalyst, and this second support is also connected to a means for heating the support. To regenerate the air cleaner, the second support is heated to a temperature at which catalytic combustion will occur. Then the first support is heated to a temperature high enough to evolve the impurities that have been absorbed on this first support. The latter temperature is usually below the temperature for catalytic combustion. The impurities evolved from the first support are swept through the second support, where they are combusted.

In another embodiment, the present invention includes two electrically heated converters (EHCs). The EHC comprises a strip of metal that is wound into a spiral, folded in a zig-zag manner, or arranged in some other configuration, so that it can be heated by electrical resistance. In this embodiment, the first and second supports are EHCs. The first EHC is coated with a hydrophobic zeolite, which is the absorbent for the impurities. The second EHC is coated with a combustion catalyst.

In still another embodiment, the air cleaner includes a heat ex-changer.

This exchanger comprises a pair of metal strips, wound into a double spiral, similar to that shown in the above-cited patent, but without a catalyst coating. The two EHCs sit within the double spiral. However, the invention also includes other embodiments in which the heat exchanger takes other forms, and does not necessarily enclose the EHC.

The EHC cleans the air flowing through it by absorbing hydrocarbons and other organic contaminants into the zeolite. Thus, the cleaning proceeds at ambient temperature. Eventually, the pores of the zeolite in the first EHC become filled with the absorbed organic contaminants. To remove the contaminants, one heats the EHCs with electric current. The contaminants evolved from the first EHC are burned catalytically in the second EHC and the air flowing towards the EHC absorbs the heat generated. The heat exchanger carries the heated air out through its outlet channel. One needs to heat only a small volume of air during regeneration, as compared with the volume of air cleaned during normal operation.

All of the foregoing applies to a closed space into which no make-up air can be brought in from the outside, and all of the cleaned air must be recycled to the closed space. For cleaning the air in a passenger airliner, the air cleaner need include only the first EHC. The cleaning step proceeds as described above, but regeneration is performed simply by heating the EHC electrically under a small flow of air, which is vented to the outside of the airliner.

The present invention therefore has the principal object of providing an air cleaner which removes organic contaminants from the air at ambient temperature.

The invention has the further object of providing an air cleaner as described above, wherein one can regenerate the air cleaner by catalytic combustion.

The present invention has the further object of providing an air cleaner especially suitable for use in enclosed spaces, such as in submarines or spacecraft.

The present invention has the further object of providing an air cleaner especially suitable for use in aircraft.

The present invention has the further object of providing an air cleaner which one can regenerate catalytically with a minimal expenditure of electrical energy.

The present invention has the further object of providing an air cleaner which can regenerate itself automatically.

The invention has the further object of increasing the efficiency of air cleaners used in aircraft, spacecraft, or submarines.

The person of ordinary skill in the art will recognize other objects and advantages from a reading of the following brief description of the drawings, the detailed description of the invention, and the appended claims.

DETAILED DESCRIPTION OF THE INVENTION

Figure 1:
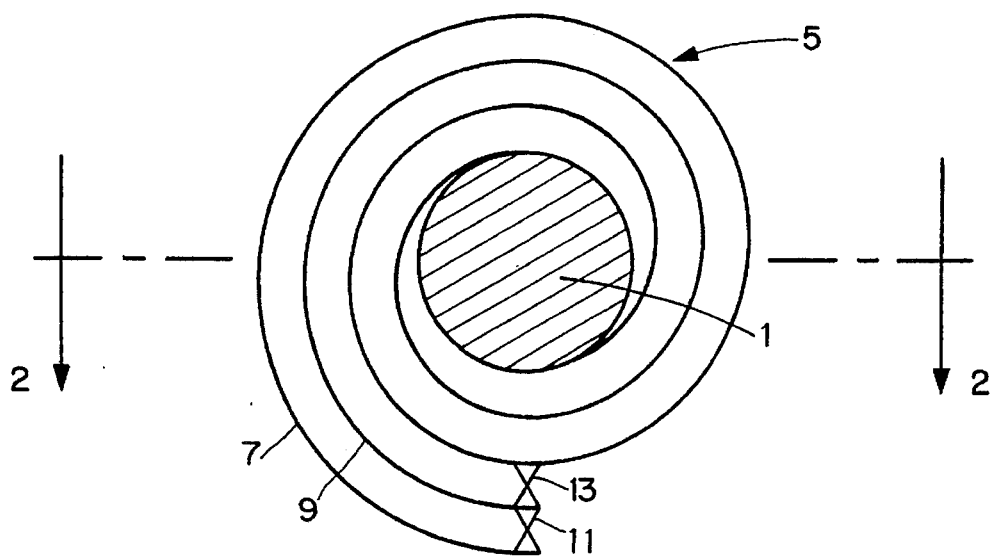
FIG. 1 shows a partially schematic, partially cross-sectional view of the air cleaner of one embodiment of the present invention.
Figure 2:
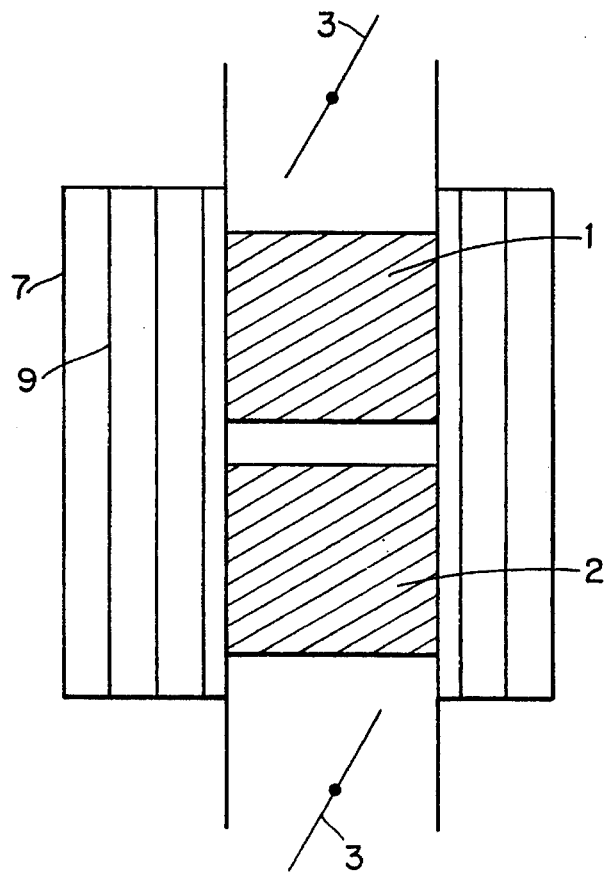
FIG. 2 shows another partially schematic, partially cross-sectional view of the air cleaner of the present invention, this view being taken along the line 2—2 of FIG. 1, and showing two electrically-heated converters arranged in series.

FIGS. 1 and 2 illustrate one embodiment of the air cleaner of the present invention. This embodiment has special utility in spacecraft, submarines, or in other enclosed spaces. The air cleaner of FIG. 1 includes a pair of electrically-heated catalytic converters (EHCs), connected in series (or "in-line"), and designated by reference numerals 1 and 2. FIG. 1 shows only EHC 1; FIG. 2 shows both EHCs. End closures 3 rotate together to open and close a path for gas flow through the EHCs.

As used in this specification, the term "EHC" means an electrically-heated converter, whether or not the converter has a catalyst coating.

The EHCs sit within double spiral 5, which comprises two metal strips 7 and 9, wound as shown. The double spiral forms a heat exchanger having an inlet channel and an outlet channel. Valve 11 controls access to the inlet channel, and valve 13 controls access to the outlet channel.

Each EHC includes one or more strips of metal wound into a spiral, formed in a zig-zag pattern, or arranged in some other pattern; FIGS. 1 and 2 do not show the arrangement of the strip(s). The present specification uses the term "honeycomb" to refer to the arrangement of the strips. It is understood that the term "honeycomb" can refer to any of the arrangements described above. What is important is that the honeycomb structure provide a support for the material described below, and that it also permit air to flow through the structure without an appreciable pressure drop.

The strips in the first EHC are coated with a material that absorbs organic compounds in preference to water vapor. This material is preferably a hydrophobic (high silica) zeolite. The strips in the second EHC are coated with a combustion catalyst, which is preferably a metal from the platinum group.

Each EHC also includes means (not shown in FIGS. 1 and 2) for applying an electric current to the strips, to heat the strips.

The EHCs can have the structure shown in U.S. Pat. Nos. 4,928,485, 4,976,929, or 5,070,694, which describe an electrically heated converter. This specification hereby incorporates by reference the disclosures of all of the above-cited patents. One can purchase EHCs from the Camet Company of Hiram, Ohio. Note, however, that the first EHC used in the present invention differs from the above-described EHCs in the composition of the coating, due to the entirely different use to which one puts the first EHC. Both EHCs of the present invention can have the same physical structure as the EHCs mentioned above.

The air cleaner of the present invention has two phases of operation, a cleaning phase and a regeneration phase. During the cleaning phase, air flows axially through the two EHCs, which are connected in series. For example, air can flow first through EHC 1 and then EHC 2. In FIG. 1, the air flows in a direction perpendicular to the paper. During the cleaning phase, the end closures 3 open to expose the EHCs to the outside, allowing air to flow through the EHCs. FIG. 2 shows the end closures in a partially open position. The zeolite (or its equivalent) on the first EHC absorbs organic contaminants in the air. During the cleaning phase, valves 11 and 13 remain closed, so that no air flows through double spiral 5. Also during the cleaning phase, no current flows through either EHC. The cleaning proceeds non-catalytically, at ambient temperature.

Eventually, the zeolite in the first EHC becomes filled with organic contaminants, and it becomes necessary to remove them. Now the regeneration phase begins. A suitable mechanical means (not shown) rotates the end closures 3 so as to block gas flow through the EHCs, isolating the EHCs from the outside. Valves 11 and 13 now open, and one applies an electric current, first to the second in-line EHC to heat it to a temperature where catalytic combustion will occur, and then to the first inline EHC. The temperature for catalytic combustion may be about 400° C., while the first in-line EHC need be heated to only about 150° C. to evolve the absorbed organic contaminants.

Now, air flows through the double spiral, entering through the inlet channel (through valve 11), flowing to the EHC, and returning through the outlet channel (through valve 13). One requires only a relatively small volume of air to complete the catalytic combustion of the contaminants, as compared with the volume of air cleaned during the cleaning phase. Thus, the flow rate of air during the cleaning phase far exceeds the flow rate during the regeneration phase.

One can achieve the desired control over the flow rate by controlling the speed of a blower. Limiting the flow rate of air during regeneration also limits the amount of electrical energy needed to heat the air. Thus, with the arrangement shown, one minimizes the heat load.

Minimizing the air flow and energy expenditure during regeneration has great importance when the cleaner operates in an enclosed environment of a submarine or a spacecraft.

Figure 3:
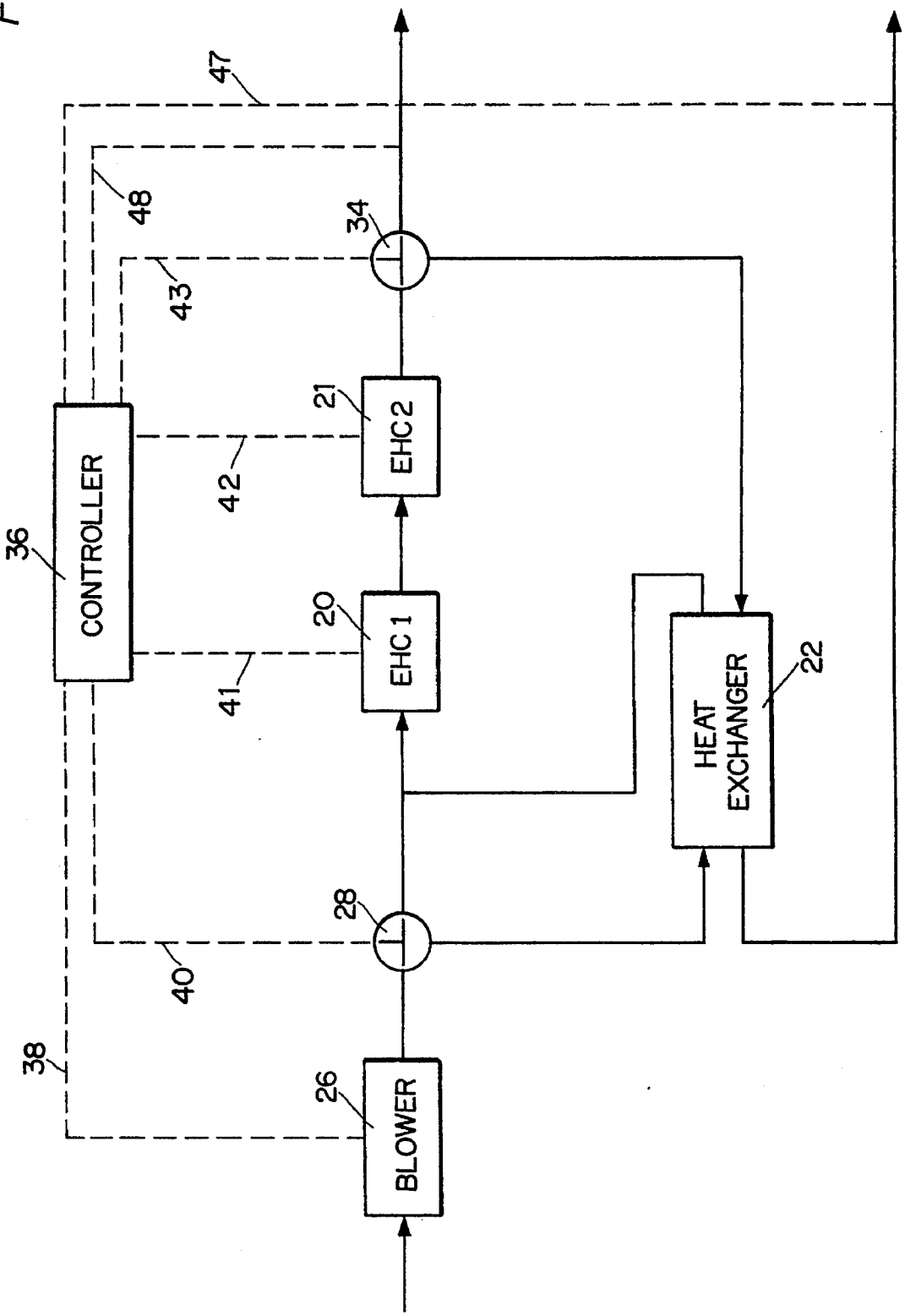
FIG. 3 shows a block diagram of the air cleaner of the present invention, with a schematic indication of the valves and controls required to operate the air cleaner.

The schematic and block diagram of FIG. 3 shows more operational details of the invention. FIG. 3 also illustrates the fact that the EHCs and heat exchanger can assume arbitrary forms. Showing the EHCs and the heat exchanger as separate blocks in FIG. 3 emphasizes the facts that these components need not have the form of a spiral, and that the heat exchanger need not physically surround the EHCs.

As shown in FIG. 3, entering air passes through blower 26, which forces air through the system. A three-way valve 28 connects the air from the blower either to EHC 20 or to heat exchanger 22. Three-way valve 34 directs air from EHC 21 either to heat exchanger 22 or back to the enclosed space containing the air to be cleaned. At the moment captured in FIG. 3, the three-way valves 28 and 34 are set to pass air directly through the EHCs. The three-way valves have another position, which can be understood by rotating the symbols in the drawings of the valves by 90° counterclockwise. In this position, valve 28 directs air from the blower into heat exchanger 22, and air from the heat exchanger enters EHC 20 and then EHC 21. Valve 34 directs air leaving EHC 21 into heat exchanger 22, and the air then leaves the heat exchanger and returns to the enclosed space containing the air to be cleaned. Note that, in the case described above, the arrows at the right-hand side of FIG. 3 represent the discharge of air to the enclosed space from which one draws air into the catalytic air cleaner. In the present case, these arrows do not indicate the venting of air to a region outside of that enclosed space.

Controller 36 controls the operations of the system. For the controller one can use a microprocessor or its equivalent.

The apparatus of FIG. 3 operates in the following manner. First, assume that the operating cycle begins with the cleaning phase. Controller 36 sets the speed of the blower at the higher level, using control line 38. The controller sets the three-way valves 28 and 34, using control lines 40 and 43, respectively, so that incoming air passes to the EHCs and not to the heat exchanger. This is the flow pattern shown in FIG. 3. The controller uses control lines 41 and 42 to turn off the electric current in the EHCs.

The cleaning phase now proceeds, with air flowing through the two EHCs connected in series. The zeolite (or equivalent) in the first EHC 20 absorbs organic contaminants from the air. The cleaning occurs at ambient temperature. During the cleaning phase, the second EHC 21 does nothing, as the air leaving the first EHC 20 simply passes through the second EHC 21 unaffected by the second EHC. Alternatively, one could put zeolite on the second EHC 21, in addition to coating it with catalyst, so that the second EHC could assist in the cleaning as well as burn the contaminants during regeneration.

In still another alternative, one could occasionally raise the temperature of the first EHC 20 to a higher than normal temperature, to burn off contaminants that were not evolved during normal operation.

While in the cleaning phase, the controller uses control line 48 to monitor the content of volatile organic compounds (VOCs) in the outlet stream exiting the second EHC 21. For this purpose, one can use a commercially available VOC sensor. As the zeolite becomes filled with organic contaminants, the VOC content of the outlet stream rises. When the VOC content exceeds a predetermined level, the controller starts the regeneration phase. To do this, the controller performs the following steps. The controller reduces the speed of the blower to minimize the flow of air during regeneration. The controller switches valves 28 and 34 so that air does not flow directly to the EHCs, but flows through the heat exchanger instead.

The controller turns on the electric current in the second in-line EHC 21, using control line 42. When the second in-line EHC 21 has reached the temperature for catalytic combustion, say, 400° C., the controller turns on the current in the first in-line EHC 20, using control line 41. The regeneration continues until control line 47 signals that the combustion products in the exiting air have fallen to some predetermined level.

Hydrocarbons that boil at 100° C. or lower will be evolved from the zeolite at temperatures of 150° C. or lower, which is usually too low for catalytic combustion. This is the reason for the two in-line EHCs, one to do the absorbing and the other to do the combusting. Thus, one heats the first EHC only to a temperature sufficient to drive off the impurities, and one heats the second EHC to a temperature sufficient to combust those impurities. The impurities driven off from the first EHC pass through the second EHC, where the impurities are burned catalytically. This is the reason for connecting the two EHCs in series.

Higher boiling hydrocarbons may not be evolved until the EHC reaches the temperature for catalytic combustion. When only high boiling contaminants are involved, it is possible to combine the two EHCs into one. Then the coating contains both the zeolite and the platinum group catalyst metal.

For cleaning the air in a passenger airliner, the air cleaner is simpler. It need include only the first EHC. This first EHC is regenerated as before by heating it electrically under a small flow of air, which is vented outside of the airliner. An airliner can have a volume of about 40,000 cubic feet. In the absence of any cleaning, this air has to be replaced five times per hour, for a total of 200,000 cubic feet per hour. Compressing the air to cabin pressure can add 5% to the fuel consumption of the jet engines. Thus, there is an incentive to clean the air and thereby reduce the frequency of replacement.

Figure 4:
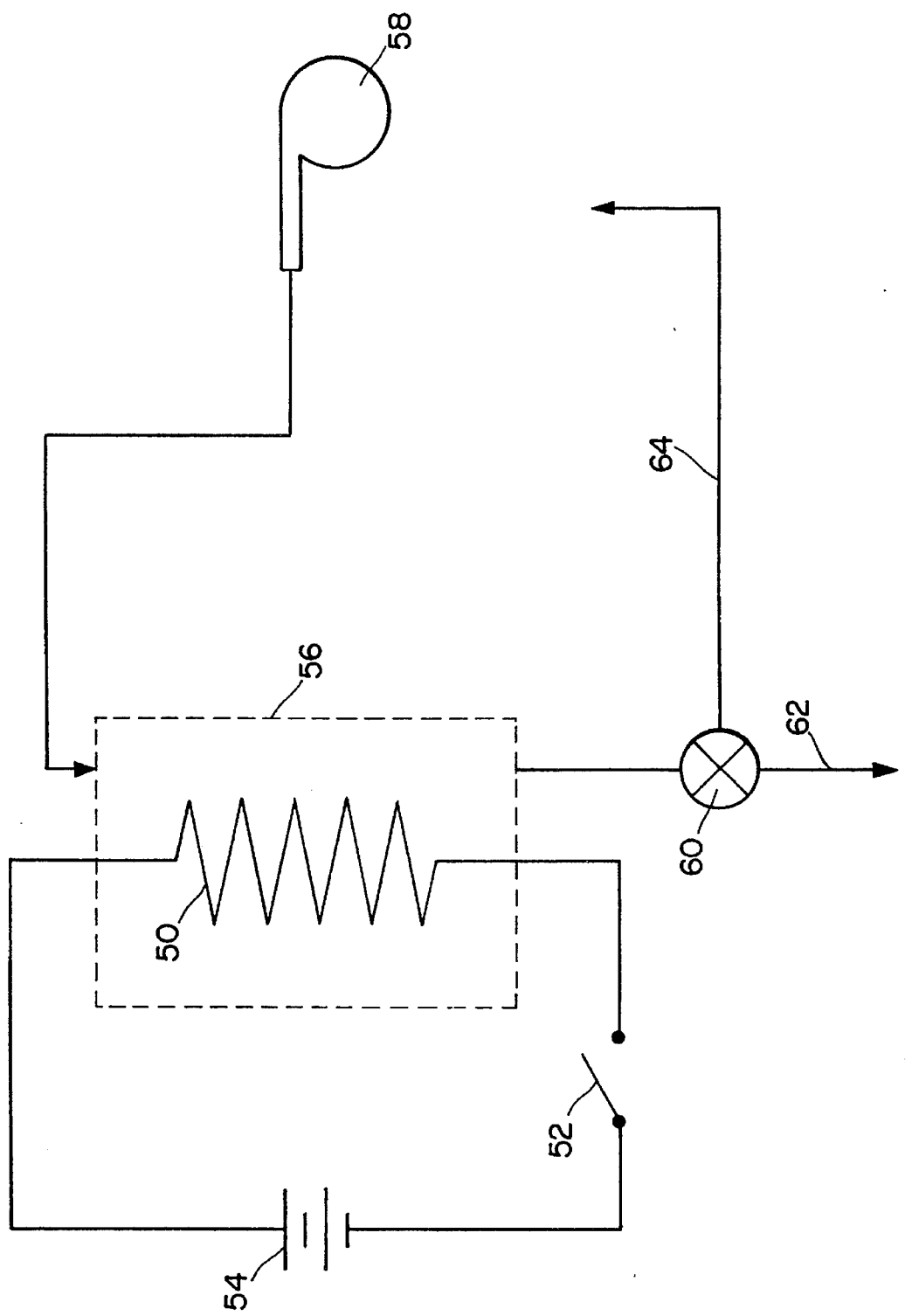
FIG. 4 shows a schematic diagram of an embodiment of the present invention intended for use in an aircraft.

FIG. 4 shows a schematic diagram of the embodiment of the air cleaner intended for use in an airliner. In FIG. 4, the EHC comprises a strip of metal 50 folded back and forth upon itself in a zig-zag manner. However, the EHC can assume any other form, such as a spiral or other configuration. Switch 52 connects battery 54 across the ends of the strip, and provides means for passing current through the strip and thereby heating the strip. The EHC sits within canister 56. Blower 58 directs air into the canister, in such manner to cause air to flow through the EHC. Air leaving the canister passes to valve 60 which directs air either into conduit 62 which vents to the region outside the aircraft, or into conduit 64, which directs the air back to the region inside the aircraft. In this embodiment, the EHC contains no catalyst, but has only a coating of zeolite (or its equivalent).

In the cleaning mode, air from the interior of the aircraft passes through the EHC and becomes cleaned due to the absorbing action of the zeolite. In the regeneration mode, one heats the EHC electrically, causing the contaminants trapped by the zeolite to evolve, and these contaminants travel, together with the air flowing out of the EHC, to the outside, through the venting conduit 62. A suitable intake conduit (not shown) draws make-up air from the outside into the aircraft cabin. In the latter embodiment, one needs only one EHC because there is no need to combust the impurities evolved from the EHC, since those impurities are vented to the outside. Also, one can omit the heat exchanger. One controls the speed of the blower by suitable conventional means (not shown).

During regeneration, one uses a smaller flow of air than during the cleaning phase.

Note also that FIG. 4, though directed to a different embodiment from those of the other figures, shows certain features which can be common to all embodiments. For example, the structure of the metal strip defining the EHCs in FIGS. 1–3 can be a zig-zag, as shown in FIG. 4. Any of the embodiments can use this structure, or other structures. FIG. 4 also shows the connection of a source of electric current to the EHC; one can use the same manner of connection in the other embodiments. Of course none of the embodiments is limited to the use of a battery; other types of current sources can be used.

The embodiment in FIG. 4 can be used to clean the air in buildings as well as in aircraft.

One can modify the invention in other ways. One should not consider the invention limited to a particular kind of coating, as one could use a synthetic zeolite, or its equivalent, or another material entirely, as the material used to absorb the organic contaminants. As noted above, the invention can employ alternative physical structures for the EHC and heat exchanger. This specification uses the term "EHC" for convenience only; as the description makes clear, one can use any support structure that bears a material capable of absorbing impurities from the air during a cleaning phase, and which can burn off the impurities, catalytically or non-catalytically, during a regeneration phase. One should consider such modifications as within the spirit and scope of the following claims.

What is claimed is:

1. An air cleaner, comprising:

a) first and second honeycombs formed from strips of metal, the first honeycomb being coated with a material that absorbs organic contaminants in preference to water vapor, the second honeycomb being coated with a combustion catalyst, and means for directing air along a first path extending through the first and second honeycombs in series, wherein air flowing along the first path and passing through the first honeycomb becomes cleansed of organic contaminants by absorption by said material, b) a heat exchanger, formed from a pair of strips of bare metal wound into a spiral, the spiral enclosing the first and second honeycombs, the spiral including inlet and outlet channels, the spiral defining a second flow path which includes the inlet channel, the honeycombs, and the outlet channel, wherein the first and second paths are distinct, and wherein the first path substantially, excludes the inlet and outlet channels of the spiral;

c) means for closing the inlet and outlet channels so as to close said second path, and means for opening said first path, such that air can flow along the first path and through the first and second honeycombs and become cleaned by passage through the first honeycomb, and d) means for closing said first path through the first and second honeycombs, means for opening the inlet and outlet channels so as to open said second path, so that air can travel trough said second path, and means for causing an electric current to flow through at least a portion of the first and second honeycombs, wherein the first honeycomb becomes regenerated by heating of the first honeycomb, and wherein organic contaminants evolved from the first honeycomb become catalytically burned in the second honeycomb.

2. The air cleaner of claim 1, wherein the organic absorbing material includes a zeolite.

3. The air cleaner of claim 1, wherein the catalyst is a metal selected from the platinum group.

4. The air cleaner of claim 1, wherein the first honeycomb also bears a catalyst.

5. The air cleaner of claim 1, wherein the second honeycomb also bears an organic absorbing material.

6. The air cleaner of claim 1, further comprising means for providing a reduced flow rate of air through the second path relative to a flow rate of air through said first path.

7. The air cleaner of claim 1, wherein the air cleaner is located in a closed environment, and wherein air flowing in both the first and second paths is taken from said environment and returned to said environment.

8. An air cleaner, comprising:

a) first and second electrically heated converters (EHCs), the first EHC including a strip of metal coated with a material that absorbs organic contaminants, the second EHC including a strip of metal coated with a combustion catalyst, the first and second EHCs being connected such that gas can flow along a first path which passes first through the first EHC and then through the second EHC, b) a heat exchanger connected to direct air along a second path, into and out of the first and second EHCs, the second path being different from the first path, wherein the first path excludes the heat exchanger, and c) control means for initiating electric heating of the first and second EHC's, and for causing air to flow through the first path, such that the air can become cleansed of organic contaminants at ambient temperature, and for causing air to flow along the second path, through the heat exchanger to the first and second EHCs and back through the heat exchanger while heating the first and second EHCs electrically to cause evolution of organic contaminants deposited on the first EHC and to cause catalytic combustion of said evolved organic contaminants in the second EHC.

9. The air cleaner of claim 8, wherein the organic contaminant absorbing material includes a zeolite.

10. The air cleaner of claim 8, wherein the catalyst is a metal selected from the platinum group.

11. The air cleaner of claim 8, further comprising means for causing air flowing through the second path to flow at a reduced rate relative to air flowing through the first path.

12. The air cleaner of claim 8, wherein the air cleaner is located in a closed environment, and wherein air flowing in both the first and second paths is taken from said environment and returned to said environment.

13. An air cleaner, comprising:

a) first and second support structures connected fluidly in series, the support structures being disposed in a first path for flow of air to be cleaned, wherein air flowing in the first path can flow first through the first support structure and then through the second support structure, the first support structure being coated with a material which absorbs organic contaminants from the air, the second support structure being coated with a combustion catalyst, b) means for heating the first and second support structures by passing an electric current through said support structures, so as to evolve organic contaminants absorbed by said material in said first support structure and to induce catalytic combustion of said organic contaminants in said second support structure.

c) a heat exchanger, d) means defining a second path which directs air from the heat exchanger to the support structures and back through the heat exchanger, the first, and second paths being different, wherein the first path excludes the heat exchanger, e) means for opening one of said first and second paths, while simultaneously closing the other of said first and second paths.

14. The air cleaner of claim 13, wherein the organic contaminant absorbing material comprises a zeolite.

15. The air cleaner of claim 13, wherein the combustion catalyst is a metal selected from the platinum group.

16. The air cleaner of claim 13, wherein the heat exchanger comprises a spiral which substantially encloses the support structures.

17. The air cleaner of claim 13, wherein the first support structure also has a coating that includes a catalyst.

18. The air cleaner of claim 13, wherein the second support structure also includes a material which absorbs organic contaminants.

19. The air cleaner of claim 13, the cleaner further comprising means for causing air flowing through the second path to flow at a reduced rate relative to air flowing through said first path.

20. The air cleaner of claim 13, wherein the air cleaner is located a closed environment, and wherein air flowing in both the first and second paths is taken from said environment and returned to said environment.

21. A method of removing impurities from air, the method comprising the steps of:

a) directing air to be cleaned along a first path which passes through first and second support structures connected fluidly in series, the first support structure bearing a material which absorbs the impurities to be removed from the air, the second support structure bearing a combustion catalyst, wherein the impurities are absorbed by said material at ambient temperature, and b) periodically regenerating the air cleaner by heating the support structures by passing an electric current through the support structures while directing air through a second path which is different from the first path, the second path extending through the support structures, so as to cause impurities which have been absorbed by said material to be evolved from the first support structure, and to cause catalytic burning of said impurities in said second support structure.

22. The method of claim 21, wherein the support structures include input and output sides in said first path, and wherein the method further comprises the step of monitoring VOC content at the input and output sides of the support structures, and wherein step (b) is performed only when the VOC content exceeds a predetermined level.

23. The method of claim 22, wherein the air being directed through the second path is directed at a lower flow rate than that of the air passing through the support structures in step (a).

24. The method of claim 21, wherein air flows through the second path, during the regenerating step, at a reduced rate relative to air flow through said first path during the directing step.

25. The method of claim 21, wherein the air cleaner is located in a closed environment, and wherein air flowing in both the first and second paths is taken from said environment and returned to said environment.

26. An air cleaner, comprising:
 a) a metal support, disposed in a first path for flow of air to be cleaned, the support being coated with a material which absorbs organic contaminants from the air,
 b) means for passing an electric current through the support so as to heat the support and to evolve organic contaminants absorbed by said material, and
 c) means for directing air along a second path which includes the support and which is different from the first path, wherein the second path is opened only when the electric current is activated.

27. The air cleaner of claim 26, further comprising valve means for directing air which has passed through the support into either a first conduit which vents to an outside environment or a second conduit which vents to an inside environment.

28. The air cleaner of claim 26, further comprising means for causing air flowing through the second path to flow at a reduced rate relative to air flowing through said first path.

29. The air cleaner of claim 26, wherein the air cleaner is located in a closed environment, and wherein air flowing in both the first and second paths is taken from said environment and returned to said environment.

* * * * *